United States Patent
Shimizu et al.

(10) Patent No.: US 6,276,939 B1
(45) Date of Patent: Aug. 21, 2001

(54) ARTIFICIAL TOOTH AND ITS PRODUCTION METHOD

(75) Inventors: Yasuhiko Shimizu, Uji; Masatoshi Inoue; Yasumichi Yamamoto, both of Kyoto, all of (JP)

(73) Assignees: Yasuhiko Shimizu, Kyoto; Tapic International Co., Ltd., Tokyo, both of (JP)

( * ) Notice: Subject to any disclaimer, the term of this patent is extended or adjusted under 35 U.S.C. 154(b) by 0 days.

(21) Appl. No.: 09/555,422

(22) PCT Filed: Dec. 1, 1998

(86) PCT No.: PCT/JP98/05389

§ 371 Date: May 30, 2000

§ 102(e) Date: May 30, 2000

(87) PCT Pub. No.: WO99/27867

PCT Pub. Date: Jun. 10, 1999

(30) Foreign Application Priority Data

Dec. 2, 1997 (JP) .................................................. 9-331505

(51) Int. Cl.$^7$ ..................................................... A61C 8/00
(52) U.S. Cl. ............................................ 433/224; 433/173
(58) Field of Search ..................................... 433/173, 224, 433/215, 172

(56) References Cited

U.S. PATENT DOCUMENTS

| 5,772,439 | * | 6/1998 | Yamaoka et al. ................. 433/201.1 |
| 5,899,936 | * | 5/1999 | Goldstein ................................. 632/2 |

FOREIGN PATENT DOCUMENTS

| 58-32759 | 2/1983 | (JP) . |
| 58-143746 | 8/1983 | (JP) . |
| 6-7381 | 1/1994 | (JP) . |
| 8-266559 | 10/1996 | (JP) . |

* cited by examiner

*Primary Examiner*—Ralph A. Lewis
(74) *Attorney, Agent, or Firm*—Peter F. Corless; Edwards & Angell, LLP

(57) ABSTRACT

The object of the present invention is to provide an artificial tooth and its production method that is not required to be joined directly to the mandibula or the maxilla, and an artificial tooth and its production method that allows both homoplastic and heteroplastic transplantation. The artificial tooth of the present invention has a layer in which extracted collagen is filled into the root canal of a homoplastic or heteroplastic permanent tooth from which cellular components of periodontal ligament, nerve and blood vessel have been removed, and an extracted collagen membrane on the surface of the root having on top of it a periodontal ligament from which said cellular components have been removed.

6 Claims, No Drawings

ARTIFICIAL TOOTH AND ITS PRODUCTION METHOD

TECHNICAL FIELD

The present invention relates to an artificial tooth and its production method.

BACKGROUND ART

A new tooth does not grow back after a permanent tooth has come out or been extracted.

Under the present circumstances, a substitute for a tooth root made of alumina ceramics, titanium and so forth is embedded in the mandibula or the maxilla, and an artificial crown molded into the shape of the crown of the target tooth is joined and fixed on top of said root substitute to be used in place of the tooth.

In the case of this method, however, since said root substitute is directly joined and fixed to the mandibula or the maxilla, there is the problem of said artificial tooth coming out as a result of being unable to withstand the repeated load applied to said artificial tooth (as a result of the patient repeatedly biting with said artificial tooth).

On the other hand, in the case of transplanting a permanent tooth, there are reports (from both animal experiments and clinical cases) of the permanent tooth taking in cases of transplanting one of the patient's own permanent teeth to another location in the patient's mouth, or so-called autotransplantation.

However, this method is limited to application to wisdom teeth only.

In addition, there have been no reports of successful cases of homoplastic or heteroplastic transplantation.

DISCLOSURE OF INVENTION

In order to improve on the current situation, the object of the present invention is to provide an artificial tooth and its production method that is not required to be joined directly to the mandibula or the maxilla, and an artificial tooth and its production method that allows both homoplastic and heteroplastic transplantation.

The inventors of the present invention determined that the reason why previous homoplastic and heteroplastic transplantations have not been successful is due to the inability to skillfully regenerate the periodontal ligament, dental pulp, nerves and blood vessels, and particularly the periodontal ligament, for transplanted artificial teeth, thereby leading to completion of the present invention.

Namely, the present invention is an artificial tooth that uses a homoplastic or heteroplastic artificial tooth from which cellular components of periodontal ligament, nerve and blood vessel have been removed, said artificial tooth having a layer in which extracted collagen is filled into the root canal(s), and a membrane of extracted collagen on the surface of the root having on top of it a periodontal ligament from which said cellular components have been removed.

Here, the phrase "from which cellular components of periodontal ligament, nerve and blood vessel have been removed" refers to the complete removal of cellular components originating in said permanent tooth that demonstrate antigenicity or are strongly antigenic from a homoplastic or heteroplastic permanent tooth that serves as the base for the artificial tooth. Since periodontal ligament removed of said cellular components, and namely periodontal ligament containing residual connective tissue present in the manner of digging vertically in the cementum of said permanent tooth, provides a foothold until regeneration of the periodontal ligament of the patient receiving transplant, along with a membrane of extracted collagen formed on top of it (which penetrates into the periodontal ligament from which said cellular components have been removed, in it's formation process), it is critically important to leave said periodontal ligament from which said cellular components have been removed to contribute to regeneration of the periodontal ligament. Furthermore, although there are many cases in which nerves and blood vessels are attached to said sampled permanent tooth, the cellular components contained therein are incidentally removed when performing removal of cellular components in said periodontal ligament. Different from periodontal ligament in which extracellular components have been intentionally allowed to remain, extracellular components of nerves and blood vessels may also be completely removed at this time.

In addition, the above-mentioned homoplastic or heteroplastic permanent tooth is an artificial tooth composed of a molded body, having a shape at least equivalent to the root and comprised of hydroxyapatite having a lumen equivalent to the root canal inside, and extracted collagen present in the gap between them, and may be an artificial tooth having a layer in which extracted collagen is filled into said lumen along with a membrane of extracted collagen on the surface of said portion equivalent to the root. This is because, although the degree of perfection of regeneration is relatively low with respect to the point of not having a periodontal ligament from which cellular components that contribute to regeneration of the periodontal ligament of the patient receiving transplant have been removed, with respect to other points, namely since necessary steps required for regeneration of the periodontal ligament of the patient receiving transplant as well as nerves and blood vessels have been taken, the object of providing an artificial tooth that is not required to be directly joined to the manndibura or the maxilla can be sufficiently achieved. Furthermore, hydroxyapatite is only selected because it is a material that is currently recognized to have the desired strength and have excellent biocompatibility. Thus, a material other than hydroxyapatite can naturally also be used provided it has strength and demonstrates biocompatibility that are greater than those of hydroxyapatite.

Furthermore, the extracted collagen layer, which is formed as a result of being filled into the root canal or lumen that is equivalent to said root canal, provides a foothold for regeneration of nerves and blood vessels of the patient receiving transplant for the transplanted artificial tooth. In addition, the extracted collagen layer formed on the surface of the root or portion equivalent to the root provides a foothold for regeneration of the periodontal ligament of the patient receiving transplant.

Thus, growth factors such as b-FGF and so forth may be additionally contained in said layer in which extracted collagen is filled and/or said membrane of extracted collagen. This is because the rate of their regeneration is accelerated.

Here, the term "extracted collagen" refers to type I collagen or a mixture of type I and type III collagen that is solubilized using acid, base or enzyme and so forth from a raw material such as skin, bone, cartilage, tendon or organs of various animals such as cows, pigs, rabbits, sheep, kangaroos or birds, while the term "their layer or membrane" refers to that having an amorphous structure in which collagen molecules are dispersed. Extracted collagen retains the inherent properties of collagen, namely excellent bioaffinity, tissue compatibility and promotion of tissue regeneration. Moreover, since antigenic groups in the form of telopeptides are removed in the solubilization procedure, it is a preferable material for the object of the present invention.

On the other hand, the above-mentioned artificial tooth can be produced in the manner described below.

In the case of using a permanent tooth sampled from a homoplastic or heteroplastic body as the base of an artificial tooth, said permanent tooth is washed with surface activator (preferably a non-ionic surface activator that is a polyoxyethylene derivative, typical examples of which include Triton X-100, Lubrol PX and members of the Tween series), and cellular components of the periodontal ligament, the nerves and blood vessels of said permanent tooth are removed (at least the extracellular components of the periodontal ligament remain). Next, extracted collagen is filled into the root canal of said permanent tooth and a membrane of extracted collagen is formed on the surface of the root having on top of it a periodontal ligament from which said cellular components are removed.

Here, washing of said tooth with surface activator is specifically performed by immersing for 12–72 hours in a surface activator solution of 0.1–3 wt %. If the concentration of surface activator is less than 0.1 wt %, the above removal of cellular components is insufficient, and if the concentration exceeds 3%, said surface activator remains behind. On the other hand, if the immersion time is less than 12 hours, said removal of cellular components is insufficient, while if the immersion time exceeds 72 hours, extracellular components of the periodontal ligament inherent to the sampled permanent tooth are destroyed. Furthermore, since nerves and blood vessels of said tooth are present in the root canal which is an extremely narrow tube, in the sense of achieving faster and adequate penetration of the surface activator solution, prior to washing said permanent tooth, the inside of the root canal may be cleaned mechanically by using a dental brush and so forth. Moreover, in the sense of being sure of a higher degree of removal of said nerves and blood vessels, ultrasonic washing may be performed before said washing and/or after said cleaning.

Next, although the filled layer and membrane of extracted collagen are formed, in the case of the latter, the above-mentioned washed artificial tooth should preferably be immersed in an approximately 3N hydrochloric acid solution containing 0.1–3 wt %, and particularly 1–2 wt %, of extracted collagen followed by air drying and the formation of a collagen layer having a thickness of preferably 10–2000 $\mu$m, and particularly 30–100 $\mu$m, on the surface of the root (and more accurately, on the periodontal ligament from which cellular components have been removed). On the other hand, in the case of the former, said collagen-hydrochloric acid solution should be introduced into the root canal by applying a method such as aspirating under a vacuum (teeth in which there are two root canals), a method in which the tip end of the crown is cut away and, after the root canal is formed into an open hole, aspirating under a vacuum (teeth in which there is only one root canal), or a method of injecting with a syringe, followed by drying said filled collagen-hydrochloric acid solution.

In addition, rapid freezing may be applied as the method for removing at least the above-mentioned cellular components in the periodontal ligament (and similar to the method using surface activator, cellular components of nerves and blood vessels originating in the sampled permanent tooth are also removed by this procedure).

Here, freezing of a sampled permanent tooth by rapid freezing is specifically performed by rapidly freezing to a temperature of −10 to −196° C., and maintaining this temperature for 1 to 48 hours. If the temperature is higher than −10° C., destruction of cellular components is inadequate, while if the temperature is lower than −196° C., the artificial tooth itself is destroyed. On the other hand, if the time during which the above temperature is maintained is less than 1 hour, destruction of cellular components is inadequate, while if the above time exceeds 48 hours, the artificial tooth itself becomes brittle. Furthermore, in this method as well, mechanical pre-cleaning of the inside of the root canal may also be performed in the same manner as the method using surface activator. In addition, ultrasonic washing may be performed before and after application of rapid freezing for the same reasons as in the method using surface activator.

On the other hand, in the case of using as the base an artificial tooth comprising a molded body made of hydroxyapatite in which a lumen equivalent to the root canal is formed inside, and extracted collagen present in the gap, filling of extracted collagen into said lumen and formation of an extracted collagen membrane on the surface of the portion equivalent to the root of said tooth should be performed in the same manner as in the case of an artificial tooth based on a homoplastic or heteroplastic permanent tooth because removal of cellular components of the periodontal ligament, and even removal of nerves and blood vessels, is not necessary. Furthermore, the artificial tooth comprising a molded body made of hydroxyapatite, which is serves as the base, and extracted collagen present in the gap is produced by kneading said hydroxyapatite as a filler and said extracted collagen as a binder (to form a clay-like substance), molding (the lumen equivalent to the root canal is formed in side either before or during molding) to the desired root shape (since the portion equivalent to the crown can use a prosthesis used in dental treatment, it is not necessary to have the overall shape of the tooth prior to transplantation), and applying heat to induce thermal dehydration crosslinking in said extracted collagen. Alternatively, said artificial tooth is produced by forming a large number of fine holes (having a diameter of at least 90 $\mu$m and preferably about 300 $\mu$m, said holes preferably being through holes) towards the lumen in the portion equivalent to the root of a hydroxyapatite sintered body having the desired root shape and said lumen equivalent to the root canal therein, and allowing said extracted collagen to seep in through said holes when forming said extracted collagen membrane on the surface of the portion equivalent to the root.

BEST MODE FOR CARRYING OUT THE INVENTION

The following provides a detailed explanation of the present invention based on embodiments of the present invention.

Embodiment 1

The lower incisor of a white domestic rabbit and the lower canine of a beagle dog were extracted without damaging the periodontal ligament after which both were respectively washed using surface activator. The conditions for said washing are as shown below (encircled numbers indicate the order of each procedure).

(1) Ultrasonic Washing
  Treatment time: 1 hour (2) Washing with Surface Activator Solution
   Chemical used: Triton X-100 (produced by Sigma)
   Concentration used: 1 wt %
   Immersion time: 72 hours (room temperature, continuous stirring)
(3) Ultrasonic Washing
   Treatment time: 1 hour
(4) Rinsing
   Treatment time: 48 hours (room temperature, under running water)

Following the above procedures, as a result of staining (using hematoxylin-eosin stain) and observing the state of residual cells in the periodontal ligament with an optical microscope, said cellular components were confirmed to have been completely removed. (Cellular components of nerves and blood cells were similarly completely removed.)

Different samples on which the above procedure was performed (that were not observed for the state of residual cells) were immersed for 60 minutes in extracted collagen hydrochloric acid solution of approximately 3 N and injected with said extracted collagen hydrochloric acid solution into their respective root canals using a syringe followed by thermal dehydration crosslinking for 24 hours at 140° C. to obtain homoplastic artificial teeth originating in the body. Incidentally, the thickness of the extracted collagen membrane formed on the surface of the root was approximately 100 m.

The resulting artificial teeth were respectively implanted in different homoplastic animals (a different white domestic rabbit from which the lower incisor had been extracted and a different beagle dog from which the lower canine had been extracted in which there were no residual periodontal ligaments in the extracted teeth of these specimens). 90 days later, said transplanted teeth were sliced into thin sections along with the mandibula. As a result of observing these thin sections with an optical microscope, it was confirmed that not only periodontal ligament but also nerves and blood vessels were confirmed to be regenerating.

Embodiment 2

With the exception of applying the rapid freezing method instead of the washing method using surface activator (procedure (2) was changed to rapid freezing, and rapid freezing conditions consisted of continuously freezing at −84° C. for 72 hours followed by thawing at 4° C. for 1 hour) and not performing procedure (4), the test to confirm the removal of cells in periodontal ligament and the test to observe the state of regeneration of periodontal ligament of the transplanted tooth (and also observed for nerves and blood vessels) were performed in the same manner as Embodiment 1.

The results were the same as those obtained in Embodiment 1 for both tests.

Industrial Applicability

According to the artificial tooth of the present invention, since the periodontal ligament of the transplanted tooth itself is regenerated between the mandibula and artificial tooth, the artificial tooth and mandibula are not required to be joined directly. Moreover, in addition to a homoplastic or heteroplastic permanent tooth, an artificial tooth comprising hydroxyapatite and extracted collagen can be used as the transplant source.

What is claimed is:

1. An artificial tooth having a layer in which extracted collagen is filled into the root canal of a homoplastic or heteroplastic permanent tooth from which cellular components of periodontal ligament, nerve and blood vessel have been removed, and an extracted collagen membrane on the surface of the root having on top of it a periodontal ligament from which said cellular components have been removed.

2. The artificial tooth according to claim 1, wherein growth factors are additionally contained in the above layer in which extracted collagen is filled and/or in the above extracted collagen membrane.

3. A production method of an artificial tooth comprising: washing a permanent tooth sampled from a homoplastic or heteroplastic body with surface activator; removing cellular components of the periodontal ligament, nerve and blood vessel from said permanent tooth; filling extracted collagen into the root canal of said permanent tooth; and forming an extracted collagen membrane on the surface of the root having on top of it a periodontal ligament from which said cellular components have been removed.

4. The method according to claim 3, wherein washing of said sampled permanent tooth with surface activator is performed by immersing said sampled permanent tooth for 12 to 72 hours in 0.1 to 3 wt % surface activator solution.

5. A production method of an artificial tooth comprising: rapidly freezing a permanent tooth sampled from a homoplastic or heteroplastic body; removing cellular components of the periodontal ligament, nerve and blood vessel from said permanent tooth; filling extracted collagen into the root canal of said permanent tooth; and forming an extracted collagen membrane on the surface of the root having on top of it a periodontal ligament from which said cellular components have been removed.

6. The method according to claim 5, wherein freezing of said sampled permanent tooth by rapid freezing is performed by rapidly freezing said sampled permanent tooth to a temperature of −10 to −196° C. and maintaining that temperature for 1 to 48 hours.

* * * * *